United States Patent
Gerstner et al.

(10) Patent No.: US 6,741,346 B1
(45) Date of Patent: May 25, 2004

(54) METHOD FOR DETECTING FLUORESCENCE PHENOMENA IN MICROSCOPE

(75) Inventors: Volker Gerstner, Jena (DE); Ralf Wolleschensky, Schoeten (DE)

(73) Assignee: Carl Zeiss Jena GmbH, Jena (DE)

( * ) Notice: Subject to any disclaimer, the term of this patent is extended or adjusted under 35 U.S.C. 154(b) by 164 days.

(21) Appl. No.: 09/869,317

(22) PCT Filed: Nov. 22, 2000

(86) PCT No.: PCT/EP00/11626
§ 371 (c)(1),
(2), (4) Date: Dec. 21, 2001

(87) PCT Pub. No.: WO01/38856
PCT Pub. Date: May 31, 2001

(30) Foreign Application Priority Data

Nov. 25, 1999 (DE) .......................................... 199 56 620

(51) Int. Cl.[7] ................................................. G01J 3/30
(52) U.S. Cl. .................................... 356/318; 250/459.1
(58) Field of Search ................................ 356/317–318, 356/417; 250/458.1–461.2; 359/368

(56) References Cited

U.S. PATENT DOCUMENTS

| | | | |
|---|---|---|---|
| 4,786,170 A | 11/1988 | Groebler | |
| 5,034,613 A | * 7/1991 | Denk et al. | ............... 250/458.1 |
| 5,459,323 A | 10/1995 | Morgan | |
| 5,485,530 A | 1/1996 | Lakowicz et al. | |
| 5,504,337 A | * 4/1996 | Lakowicz et al. | ........ 250/461.2 |

FOREIGN PATENT DOCUMENTS

| | | |
|---|---|---|
| DE | 3 614 359 | 2/1987 |
| DE | 41 04 014 | 8/1991 |
| DE | 42 31 477 | 3/1994 |
| WO | WO 98/09154 | 10/2000 |

OTHER PUBLICATIONS

J. Pawley (Ed.), *Handbook of Biological Confocal Microscopy*, Chapters 28 and 31 (New York: Plenum Press, 1995).
X. Wang and B. Herman (Eds.), *Fluorescence Imagin Spectroscopy and Microscopy*, vol. 137, Chapters 8–11 (New York: John Wiley & Sons, Inc., 1996).
K. Dowling et al., "Two Dimensional Flourescence Lifetime Imaging using a 5 kHz/110 ps Gated Image Intensifier," Kentech Instruments Ltd. (www.kentech.co.uk/pdf_files/K_Dowling_et_al.pdf) (Oct. 24, 199).
P.T.C. So, *Timer–resolved fluorescence microscopy using two–photon excitation*, Bioimaging, 3 (1995) 49.
H. Schneckenburger, et al., *Time–gated microscopic imaging and specrtoscopy in medical diagnosis and photobiology*, Optical Engineering, 33 (8) 2600 (1994).
R. Cubeddu, et al., *A real time system for Fluorescence Lifetime Imaging*, SPIE vol. 2976, (1997) 98.
P.C. Schneider, et al., *Rapid acquisition, analysis, and display fluorescence lifetime–resolved images for real–time applications*, Rev. Sci. Instrum., 68 (11) (1997) 4107.
E. Gratton et al., *A Continuously Variable Frequency Cross Correlation Phase Fluorometer with Picosecond Resolution*, Biophys. . J. 44 (1983) 315.
E. Gratton, *Multifrequency Phase and Modulation Fluorometry*, Ann. Rev. Biophys. Bioeng. 13 (1984) 105.

* cited by examiner

*Primary Examiner*—F. L. Evans
*Assistant Examiner*—Kara Geisel
(74) *Attorney, Agent, or Firm*—Jacobson Holman PLLC

(57) ABSTRACT

Process for detecting the phenomenon of fluorescence in a microscope, wherein the sample is irradiated by a modulated and/or pulsed laser light source, and the fluorescence is detected at least in two different phase positions of the detector.

38 Claims, 2 Drawing Sheets

US 6,741,346 B1

METHOD FOR DETECTING FLUORESCENCE PHENOMENA IN MICROSCOPE

BACKGROUND OF THE INVENTION

1. Field of the Invention

The process that is presented relates to confocal and 2-photon fluorescence microscopy as described by M. G öppert-Mayer, Ann. Physik 9, 273 (1931) and T. Wilson, *Theory and Practice of Scanning Optical Microscopy* (Academic Press, 1984). Both methods are assumed to be known.

Both confocal fluorescence microscopy and 2-photon microscopy are modified by the method described below to the extent that an additional contrast parameter is possible: the fluorescence lifetime.

2. Related Art

Temporal resolved fluorescence and/or the use of the lifetime as a contrast parameter in confocal/2-photon microscopy can be carried out by two different methods—by time domain detection and frequency domain detection.

In the case of time domain detection (described in Published patent application DE 41 04 014 of Wabnitz, entitled "Method for Determining the Calcium Concentration in Cells"; and in Patent DE 36 14 359 C2 of Gröbler, entitled "Device for the Analysis and Imaging of Real Time Intensity of Fluorescence Radiation resulting from Point-by-Point Excitation of a Preparation by means of Laser Light") a fluorescent sample is excited so as to produce fluorescence by means of a pulsed light source, and the fluorescence emission is detected with time resolution either by means of time correlated single photon counting (TCSPC)(described in Patent WO 98/09154 to Müller et al., entitled "System for Differentiating Fluorescing Molecular Groups by means of Time-Resolved Fluorescence Measurement"; and in Published patent application DE 42 31 477 A1 of Han, entitled "Method for Optical Sorting of Plastics by means of Time-Resolved Laser Spectroscopy") or by means of time gated detection (described by H. Schneckenburger et al., "Time-Gated H. Microscopic Imaging and Spectroscopy in Medical Diagnosis and Photobiology," *Optical Engineering* 33 (8) 2600 (1994); R. Cubeddu et al., "A Real Time System for Fluorescence Lifetime Imaging," *SPIE* 2976 (1997) 98; and K. Dowling et al., "Two Dimensional Fluorescence Lifetime Imaging using a 5 kHz/110 ps Gated Image Intensifier" (www.kentech.co.uk/pdf_files/K_Dowling_et_al.pdf)).

In the case of frequency domain detection, a fluorescent sample or preparation is excited with a light source that is either actively modulated or pulsed (for example, by means of passive mode coupling). Since any arbitrary modulation of the excitation by means of a Fourier analysis breaks down into sinusoidal components, the observation of a sinusoidal excitation is adequate. The frequency domain detection technique is based on the delay of the fluorescence emission by a phase f and a change in the modulation depth M compared with the excitation light as a function of the modulation frequency $\omega(=2\pi f_{mod})$ and the lifetime $\tau$.

$$\phi = a\tan(\omega\tau) \quad (1)$$

$$M = \frac{1}{\sqrt{1+\omega^2\tau^2}} \quad (2)$$

However, the resulting fluorescence signal, oscillated with the modulation frequency, is out of phase and demodulated. For typical fluorescence lifetimes ranging from $\tau = 1 \ldots 10$ ns, modulation frequencies ranging from $f_{mod} = 10 \ldots 100$ MHZ are adequate.

Since it generally does not make any sense to scan the fluorescence signal at such high modulation frequencies, a frequency mixing process is used to detect the signal. For mixing, any detection element with a modulatable amplification is suitable.

In essence two methods are distinguished—the homodyne and the heterodyne detection techniques.

To understand the principle, one observes generally two "signals" $S_1$, $S_2$, (where, for example $S_1$ is modulated excitation, and $S_2$ is modulated amplification).

$$S_1 = A_0 + A_1 \cos(\omega_a t + \alpha)$$

$$S_2 = B_0 + B_1 \cos(\omega_b t + \beta) \quad (3)$$

Multiplication results in:

$$S_1 S_2 = A_0 B_0 + A_0 B_1 \cos(w_b t + b) + B_0 A_1 \cos(w_a t + a) + A_1 B_1 \{\cos((w_a w_b)t + (a+b)) + \cos((w_a w_b)t + (a-b))\} \quad (4)$$

Homodyne Detection

If $\omega_a = \omega_b$ (homodyne), the second harmonic and a frequency independent component are generated by the mixing process of the "signals" $S_1$ and $S_2$. A low pass filter results in a suppression of the components at $\omega_a$ and $2\omega_a$. Only the DC background and the phase dependent DC component are detected. The signal, filtered by means of a low pass (LP) filter, can be written as:

$$LP(S_1 S_2) = A_0 B_0 + A_1 B_1 \cos(\alpha - \beta) \quad (5)$$

In the case of homodyne detection this frequency independent (DC) signal can be detected in multiple relative phases. To measure the fluorescence lifetime, at least 3 three different phase positions are necessary. At just two relative phase positions, the phase shift or the demodulation, induced by the fluorescence lifetime, can be used as the contrast parameter (as described by P. C. Schneider et al., "Rapid Acquisition, Analysis and Display of Fluorescence Lifetime Resolved Images for Real time Applications," *Rev. Sci. Instrum.* 68 (11) 4107 (1997) (hereafter, "Schneider et al.")).

Heterodyne Detection—Cross Correlation

If $\omega_b = \omega_a + Dw$ (heterodyne), the mixing process generates a high frequency signal at the total frequency and a signal at the cross correlation frequency $\Delta\omega$. Again the high frequency components are suppressed by a low pass filter.

$$LP(S_1 S_2) = A_0 B_0 + A_1 B_1 \cos(\Delta\omega t + \alpha - \beta) \quad (6)$$

In the case of heterodyne detection, the differential frequency $\Delta\omega$ is detected. Phase position and modulation depth of the signal at the differential frequency make it possible to determine the lifetime. Typical cross correlation frequencies range a few Hz up to about 100 kHz.

A more comprehensive presentation of the heterodyne method can be found in the publication by E. Gratton et al., "A Continuously Variable Frequency Cross Correlation Phase Fluorometer with Picosecond Resolution," *Biophys. J.* 44 (1983) 315 (hereinafter, "Gratton"), and "Multifrequency Phase and Modulation Fluorometer, " *Ann. Rev. Biophys. Bioeng.* 13 (1984) 105 (hereinafter, "Gratton 2").

In both the homodyne and heterodyne detection technique the high frequency change is reflected, so to speak, on the low frequency range.

Owing to the multi-exponential decay behavior of the fluorescence emission, the lifetimes, determined from the modulation depth and the phase shift, vary. Therefore, for precise measurement of the lifetime, the excitation frequency has to be varied as described by Gratton 2.

If, in contrast, the lifetime is supposed to be used, for example, as a contrast parameter in an imaging process, this is generally not necessary. Frequently it suffices, for example, to show the phase shift or the demodulation by means of the lifetime or by means of the lifetime, calculated from the phase shift and demodulation data, at a fixed modulation frequency.

BRIEF DESCRIPTION OF THE DRAWINGS

The invention is better understood by reading the following Detailed Description of the Preferred Embodiments with reference to the accompanying drawing figures, in which like reference symbols refer to like elements throughout, and in which.

DETAILED DESCRIPTION OF THE PREFERRED EMBODIMENTS

1.1 One Photon Confocal Lifetime Imaging, Homodyne

Figure 1:
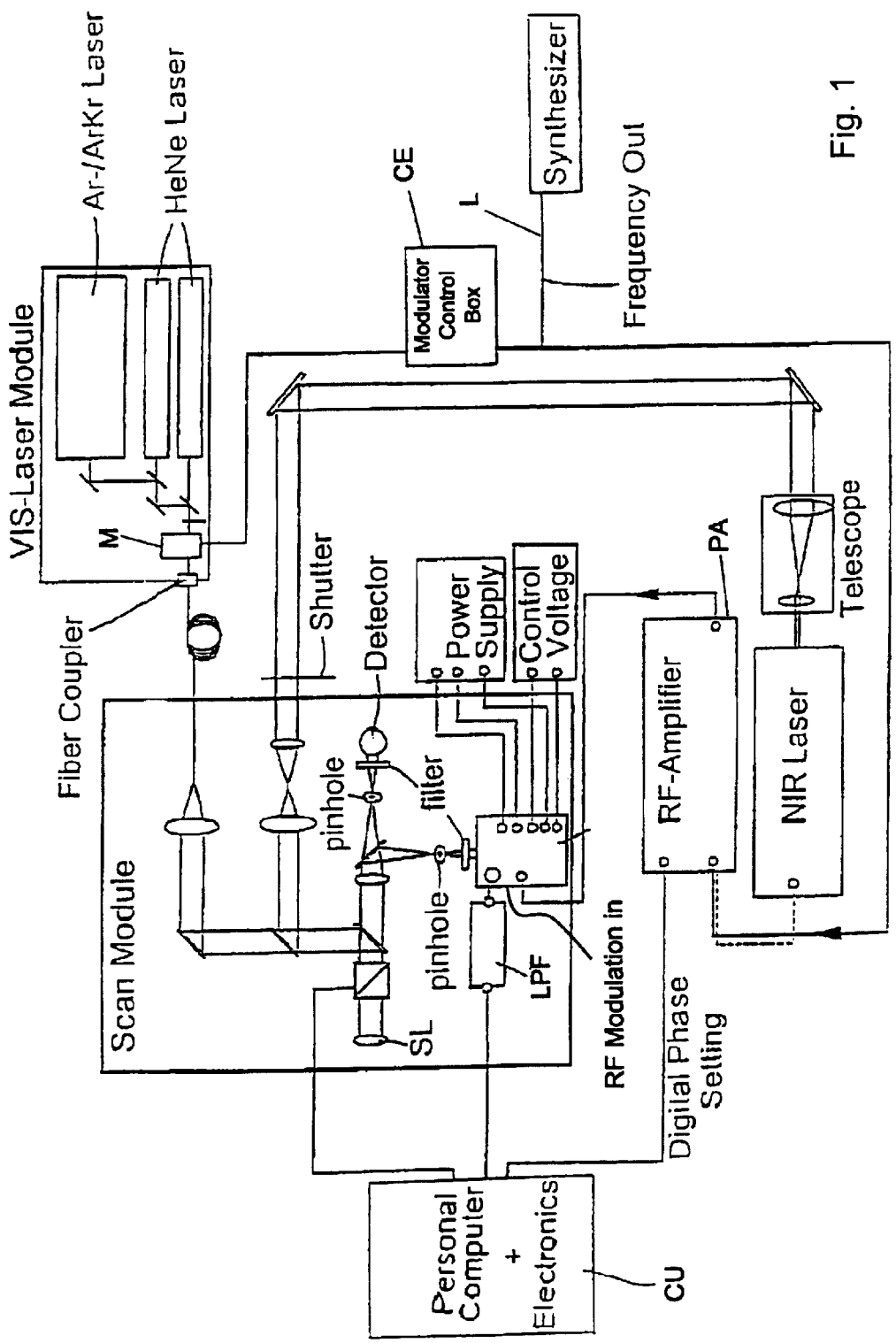
FIG. 1 is a schematic diagram showing apparatus for detecting fluorescence in a microscope in accordance with the present invention.

The confocal design of a laser scanning microscope (LSM) is modified for lifetime imaging to the extent that the excitation light source is modulated or a pulse laser is used.

the amplification of the detector (for example, a photomultiplier tube (PMT)) is modified.

an electronic phase shifter is used that permits the relative phase position of light excitation and detection to be adjusted. This circuit with the components that are used is shown in FIG. 1.

First Embodiment

Driven by means of a synthesizer S using a quartz crystal, RF frequencies are generated in the range from 10 to 100 MHZ. The output of the synthesizer S is connected, on the one hand, over a shielded high frequency line (for example, over a BNC cable) to a phase shifter/amplifier PA. The phase shifter/amplifier PA amplifies, on the one hand, the high frequency input signal of the synthesizer—in the first embodiment, to a power of approximately 1.5 W at a resistance of 50 W. Furthermore, the phase position of the amplified RF signal can be varied with the phase shifter/amplifier PA. The relative phase of the phase shifter/amplifier PA can be adjusted digitally over a control line, for example, by means of a control via a serial interface of a PC. The amplified RF signal is fed to a modulated PMT, designated PMT1 in FIG. 1—for example, the PMT module (H 6573) of Hamamatsu, the "Technical Information" for which contains a detailed presentation of the operating mode. The amplified RF voltage (approximately 25 $V_{pp}$/50 W) is fed in the PMT to the second dynode and used to modulate the amplification of the PMT. To produce a defined low pass filter, the output signal of the PMT can be smoothed by means of a commercial low pass (LP) filter LPF. The 3 dB threshold frequency $f_g$ of the LP filter LPF is selected in such a manner that 1/pixel dwell time $<<f_g<<f_{laser}$ where $f_{laser}$=the laser modulation frequency. The signal filtered thus is fed to the standard detection electronics of the laser raster microscope (LRM). (For greater comprehension: in principle, for example, to an ADC (analog digital converter), which is synchronized with the xy scanners XYS of the LRM.

A second identical output of the synthesizer S is also connected to the control electronics CE of the light modulator M by means of a high frequency line L. An acousto-optical modulator (or an electro-optical modulator) can be used, for example, as the modulator M in the laser beam path. The light modulator M is a component of the laser module of the confocal laser raster microscope. Such a design makes it possible to vary the rotative phase position of the phase shifter/amplifier PA and the light modulator M. The frequencies for the light modulator M for modulating the laser light and the PMT amplification voltage are identical. The phase position generally varies. At least the phase of an RF output can be adjusted digitally in about 1° steps. In the case depicted in FIG. 1, the phase of the PMT modulation voltage is varied in the phase shifter/amplifier PA by means of the phase shifter.

The operating mode and the related advantages of the method in accordance with the first embodiment will now be described.

Using the conventional LSM design, the light of the modulated/pulsed laser light source is focused on the lens plane by means of the scan mirrors and the LSM scan optics. The fluorescence is focused, as in the confocal Zeiss LSM510, in the direction of reflection on the detection pin hole using a beam splitter, focusing lens, etc. The raster-shaped movement of the laser focus over the lens plane and the synchronized detection—in the now modulated—PMT result in a confocal image of the lens plane. By using the homodyne technique, the PMT signal at the output of the LP filter LPF (image 1) is a DC signal, which varies only as a function of the laser spot position (pixel). Through repeated scanning operations during multiple different relative phases of the light modulator and detection modulation, it is possible to detect the fluorescence lifetime contrast or to measure the fluorescence lifetime. The significant advantage lies in the fact that the conventional data acquisition unit of the LRM can be used. The lifetime contrast is calculated from image to image.

Image digitizing to produce the lifetime contrast in a confocal microscope image and/or to display the confocal lifetime distribution of dyes is carried out in accordance with the following steps.

In a first step in the embodiment presented here, a first phase of the PMT detector PMT1 is adjusted digitally. The adjustment is done, as described above, with the electronic phase shifter/amplifier PA; and the resulting DC signal of the PMT (following the usual conversion from current to voltage and the usual conversion from analog to digital) is registered by means of the usual (LSM) analysis electronics in synchronism synchronization with the scanner XYS and stored in the PC by means of a storage medium.

In at least a second step the process is repeated with a second different relative phase position.

The at least two digital images are displayed, for example, by means of a computer screen without any further calculation.

For the presentation, images, generated with the following Fourier expansion algorithms, are also displayed on the screen:

The Fourier expansion is expressed by $$I(\phi+\phi_\tau)=a_0+a_1\cdot\sin(\phi)+b_1\cdot\cos(\omega) \quad (7)$$

with the fluorescence intensity of a pixel I and the corresponding Fourier coefficients $a_0$, $a_1$, $b_1$, where.

$$a_0 = \bar{I} = \frac{1}{N}\sum_{n=0}^{n-1} I\left(\varphi_\tau + n\frac{2\pi}{N}\right) \quad (8)$$

$$a_1 = \frac{2}{N}\sum_{n=0}^{n-1}\sin\left(\frac{2\pi n}{N}\right)I\left(\varphi_\tau + \frac{2\pi}{N}\right)$$

$$b_1 = \frac{2}{N}\sum_{n=0}^{n-1}\cos\left(\frac{2\pi n}{N}\right)I\left(\varphi_\tau + n\frac{2\pi}{N}\right)$$

At the same time $a_0$, $a_1$, $b_0$ are the Fourier coefficients (per pixel), N>=2 the number of the stored phase images (or pixel intensity) I=I ($\phi$).

The modulation depth $M_\tau$ and the phase shift can be expressed by the lifetime $\phi_\tau$ using the Fourier coefficients.

$$M_\tau = \frac{\sqrt{a_1^2+b_1^2}}{a_0} = \frac{1}{\sqrt{1+\omega^2\tau^2}} \quad (9)$$

$$\varphi_\tau = -1\cdot\frac{a_1}{b_1} = \omega\tau \quad (10)$$

The modulation depth M is calculated pixel by pixel. M=M (i,j)=$M_{ij}$, (i,j, pixel indices). Similarly the phase shift $\phi=\phi(i,j)=\phi_{ij}$.

The image of the modulation depth $M_{ij}$, which is calculated pixel by pixel in this manner, and the phase shift $\phi_{ij}$, are displayed on the monitor.

Another type of display is the $\tau$ imaging, that is the lifetime $\tau(M)_{ij}$ or $\tau(\phi)_{ij}$, calculated for $\tau$ by means of resolution equations (9) or (10), as described by Schneider et al.

$$\tau(M) = \frac{1}{\omega}\cdot\sqrt{\frac{1}{M^2}-1} \quad (11)$$

$$\tau(\varphi) = \frac{1}{\omega}\tan(\varphi) \quad (12)$$

M and $\phi$ are calculated with the equation (9) or (10); and the Fourier coefficients $a_0$, $a_1$, $b_1$, determined with equation (8), are calculated.

To increase the accuracy in determining the phase, it is also possible to use the optimized algorithm, presented in a paper, "Phase Evaluation by Folding," by Küchel, 1989.

Second Embodiment

Another embodiment of a confocal microscope with lifetime contrast or for the measurement of the lifetime distribution in a confocal split image can be achieved using pulse lasers. Suitable are, for example, pulse laser diodes or other, for example femtosecond (fs) laser systems (for example, a Ti:sapphire laser), for example with a downstream frequency conversion unit (for example, frequency doubling, tripling). When pulse lasers are used, there is no need to generate the RF driver frequency with synthesizers. Instead, an electronic diode signal of the pulse laser is provided (for example, PD signal out of the fs/ps NIR laser in FIG. 1 or an equivalent construction with exchange/expansion of the VIS laser module, for example with a ps diode laser etc.). The resulting RF signal of the (sufficiently fast) photodiode is a priori synchronized with the laser excitation. The RF signal can be used analogously with the RF signal of a synthesizer. That is, the phase shifter/amplifier PA is made available at the corresponding input (by way of an RF line). The rest of the process is analogous to that of the first embodiment. What is advantageous here is, on the one hand, the use of a pulse-shaped light source and the associated improvement of the signal-to-noise ratio in a lifetime contrast, generated thereby, as compared to the sinusoidal modulation of the laser excitation in the first embodiment and, on the other hand, the omission of a synthesizer for generating the RF frequency. The fluorescence is detected after a 1 photon excitation (linear in the excitation intensity).

1.2 Two Photon Confocal Lifetime Imaging, Homodyne

A third embodiment, using the combination of 2-photon microscopy with the homodyne detection technique for lifetime imaging, will now be described.

The combination of time resolution and 2-photon microscopy was already demonstrated by Gratton with the so called heterodyne technique, as described by So et al., "Time Resolved Fluorescence Microscopy using Two Photon Excitation," *Bioimaging* 3 (1995) 49 (hereinafter, "So et al."). In the heterodyne technique an fs laser is used for fluorescence excitation in a 2-photon microscope; and the PMT detector is driven at a slightly different modulation frequency. The typical repetition rate of fs Ti:sapphire lasers is in the 80 MHZ range. In the So et al. article, a frequency of 80 MHZ+25 kHz is used for amplification modulation of the PMT detector. The consequence is a beat. This beat is digitized with an analog to digital conversion (ADC) card and scanned. Thus, it is possible to detect pixel by pixel the phase shift from excitation to fluorescence (heterodyne method).

In the design in accordance with the present invention, the phase shift is determined, compared to that described by So et al., not pixel by pixel, but rather image by image. That is, first one image is captured during a relative phase shift $\phi 1$ and stored. In at least one other step, an image is generated during another different relative phase $\phi 2$ (homodyne method).

The diverse images for presenting the contrast are calculated in the same manner as described above in connection with the one-photon homodyne detection technique for confocal lifetime imaging.

The procedure by which 2-photon microscopy is combined with the homodyne detection technique for lifetime imaging will now be described.

A dyed or self-fluorescing sample is excited so as to emit fluorescence by way of two photon absorption. The pulsed laser can be, for example, a Ti:sapphire laser (also sums with double or triple frequency or a difference with mixed frequency, etc.), a ps laser diode or a laser, which is modulated, for example, by means of an optical modulator M, such as an acousto-optical modulator (AOM) or an electro-optical modulator (EOM). In the first and second embodiments, the physical process is a one photon excitation; in the third embodiment, it is two photon excitation (or in general multiphoton excitation). To excite the fluorescence in the embodiment according to FIG. 1, an fs Ti:sapphire laser is used. The repetition rate of the fs laser is approximately 80 MHZ, non-linear optics laser scanning microscope (NLO-LSM), fluorescence detection method).

For detection, a modulatable PMT detector from Hamamatsu (H6573) is used. The sinusoidal modulation frequency is generated from a photodiode signal of the laser (fs Mira, Coherent Corporation) by way of an emitter coupled logic (ECL) logic circuit and amplified to an average power of 15. W at 50 W by means of an RF amplifier, integrated into the phase shifter/amplifier PA, and is available at the output "RF out" of the PA. The phase of the generated sine (and thus the amplified sine) can be adjusted to approximately 1° (analogous to the first and second embodiment). The electronic jitter is <100 ps ((FIG. 1), phase shifter/RF amplifier). With the amplified sine wave at the frequency, corresponding to the laser repetition rate ($f_{rep}=f_{mod}$), the amplification of the PMT detector is modulated. To this end, the amplified RF frequency is made available to the input of the PMT module, called "RF modulation in" in FIG. 1. The current at the output of the PMT detector is smoothed with a passive LP filter or is integrated by a different method by way of the integration circuit. The resulting DC signal is made available again to the detection unit of an LRM. The rest of the procedure for gathering and evaluating the data is analogous to that described in connection with the first and second embodiments.

The distinction with respect to the first and second embodiments lies in the fact that in one case a two photon (NLO) LSM is combined with the lifetime imaging. That is, the fluorescence excitation occurs with an fs or ps pulse laser. Thus, another significant difference is the type of fluorescence excitation (here two or generally multiphotons (>2) excitation).

1.3 Arrangement for Phase Sensitive Fluorescence Detection in a Laser Scanning Microscope For two or multiphoton excitation, it is possible to use more efficient detection units due to the depth discriminated excitation. They are described in the literature under the collective term of non-descanned detection units.

Figure 2:
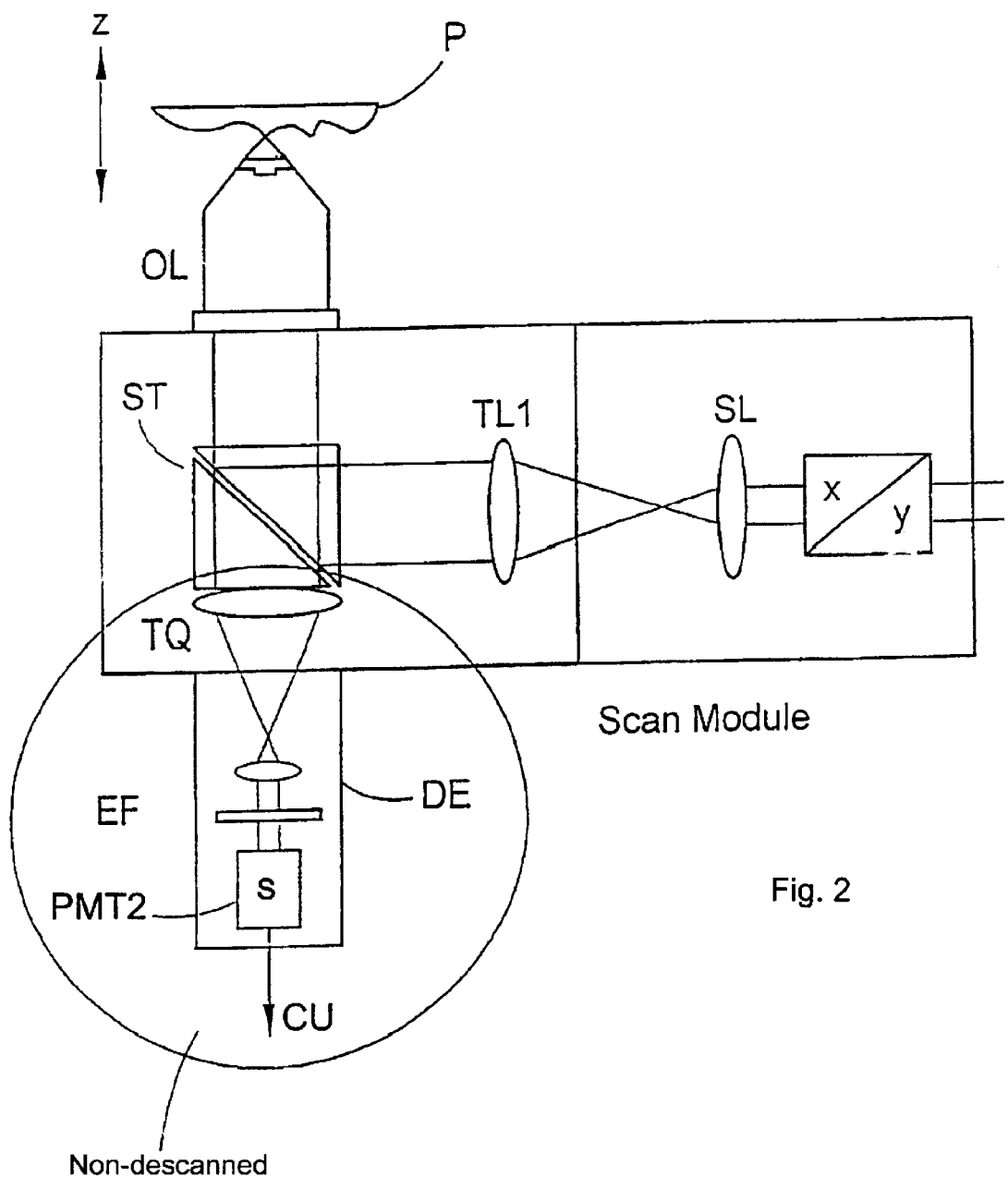
FIG. 2 is a schematic diagram showing a scan unit and a non-descanned detection unit.

This detection unit is shown in FIG. 2 as a schematic drawing, which is attached to the scan lens SL and the scanner XYS of FIG. 1 and depicts a microscope beam path, with the sample P, the lens OL, the beam splitter ST for coupling in the illumination/coupling out the radiation, coming from the sample, as well as a first tube lens TL1.

By way of a second tube lens TQ, another modulatable PMT, designated PMT2 in FIG. 2, is used for direct detection in a detection beam path DE, that is, not by way of a scan beam path.

This PMT is connected to the control unit CU in FIG. 1 and by way of said control unit CU to other units in FIG. 1.

A significant drawback with these detection units is generally their higher sensitivity to room light. Since the room light is generally not modulated, or is modulated differently from excitation light, the use of phase sensitive detection units for suppressing the room light is logical. Thus, there is no need for an expensive encapsulation of the detection unit. The configurations for one and two or multiphoton excitation have already been described above and are totally transferable to a phase sensitive detector. However, in the phase sensitive detection technique the reference signal (excitation light) and the measurement signal (fluorescence signal) have the same modulation. For most of the TiSa laser system that are used, this modulation is 80 MHZ. Thus, homodyne detection takes place. For phase sensitive detection, both signals are multiplied together in a multiplier with a fixed variable phase relation. In an advantageous arrangement the first dynode of a modulatable photomultiplier (H6573) functions as the multiplier.

The reference signal is generated from the above described phase shifter/RF amplifier PA. The clock for the phase shifter is the photodiode signal of the pulse laser. In addition, the repetition rate, predetermined by means of the pulse laser, can be expanded to a variable beat frequency range by "beating" the laser light with an optical modulator M (see FIG. 1). The beat frequency is provided by means of a synthesizer with variable phase, which is controlled by means of trigger signals of the excitation light source (see FIG. 1). The phase relation between the reference signal and the measurement signal is adjusted in such a manner that the phase shift is zero. Thus, the variable is demodulated. In this manner a DC or low frequency modulated measurement signal is obtained. However, disturbances, like room light, are highly modulated after the multiplier (like the reference signal approx. 80 MHZ). Due to the downstream low pass filter the highly modulated portions (disturbances) are filtered out and thus suppressed. An example of the low pass filter is the detection electronics of a conventional LSM.

The advantage of the described arrangement lies in the fact that the electronics on the detection side has to be designed only for low frequency signals, since the demodulation takes place photomultiplier.

What is claimed is:

1. A process for detecting the phenomenon of fluorescence in a microscope, comprising the steps of:
   irradiating a sample by at least one of a modulated and a pulsed laser light source so as to produce fluorescence, and
   detecting the fluorescence with a detector having variable phase positions, at least in two different phase positions of the detector, using a detector with a modulatable amplification.

2. The process, as claimed in claim 1, further comprising the step of generating an image for each phase position using a signal output by the detector.

3. The process, as claimed in claim 2, further comprising the step of displaying the image generated for each phase position on a monitor.

4. The process, as claimed in claim 1, wherein said steps of irradiating and detecting are carried out using a laser scanning microscope.

5. The process, as claimed in claim 1, wherein said detecting step is carried out using a modulatable PMT as the detector.

6. The process, as claimed in claim 1, wherein said irradiating step is carried out using multiphoton excitation of fluorescence emission.

7. The process, as claimed in claim 1, wherein said irradiating step is carried out using a cw laser, modulated by means of an acousto-optical modulator (AOM).

8. The process, as claimed in claim 1, wherein said irradiating step is carried out using a cw laser, modulated by means of a Pockel cell.

9. The process, as claimed in claim 1, wherein said irradiating step is carried out using a pulse laser, which is additionally modulated.

10. The process, as claimed in claim 1, wherein said irradiating step is carried out using a pulse laser, which is additionally modulated by means of an acousto-optical modulator.

11. The process, as claimed in claim 1, wherein said irradiating step is carried out using a pulse laser, which is additionally modulated by means of a Pockel cell.

12. The process, as claimed in claim 1, wherein said detecting step is carried out using time resolution and wherein said irradiating step is carried out using a multiphoton process.

13. The process, as claimed in claim 1, wherein said irradiating step is carried out using a pulsed near infrared laser.

14. The process, as claimed in claim 1, wherein said irradiating step is carried out using a pulsed near infrared laser, and further comprising the step of:

converting the frequency of the laser downstream to 1 photon excitation.

15. The process, as claimed in claim 1, wherein said irradiating step is carried out using a pulsed near infrared laser, and further comprising the step of:

converting the frequency of the laser downstream to 1 photon excitation of fluorescence.

16. The process, as claimed in claim 1, wherein said detecting step is carried out using phase sensitive detection for improving the signal to noise ratio.

17. The process, as claimed in claim 2, further comprising the step of carrying out a mathematical algorithm on the image to produce another image.

18. The process, as claimed in claim 1, wherein said irradiating step is carried out using two photon excitation.

19. The process, as claimed in claim 12, wherein in said irradiating step, the multiphoton process is second harmonic generation on surfaces.

20. The process, as claimed in claim 12, wherein in said irradiating step, the multiphoton process is two photon excitation.

21. A process for detecting the phenomenon of fluorescence in a microscope, comprising the steps of:

irradiating a sample using at least one of a modulated and a pulsed laser light source so as to produce fluorescence, multiplying a reference signal, corresponding to the at least one of the modulated and pulsed laser, and a measurement signal, corresponding to a modulated detection of the fluorescence, together with a fixed variable phase relation to obtain a result; and using the result to display an image.

22. The process, as claimed in claim 21, wherein the phase relation between the reference signal and the measurement signal is adjusted in such a manner that the phase shift is zero.

23. The process, as claimed in claim 21, wherein said detecting step is carried out using non-descanned detection.

24. The process, as claimed in claim 22, wherein said detecting step is carried out using non-descanned detection.

25. The process, as claimed in claim 21, wherein said irradiating step is carried out using multiphoton excitation of fluorescence emission.

26. The process, as claimed in claim 21, wherein said irradiating step is carried out using two photon excitation.

27. The process, as claimed in claim 21, wherein said irradiating step is carried out using a cw laser, modulated by means of an acousto-optical modulator.

28. The process, as claimed in claim 21, wherein said irradiating step is carried out using a cw laser, modulated by means of a Pockel cell.

29. The process, as claimed in claim 21, wherein said irradiating step is carried out using a pulse laser, which is additionally modulated.

30. The process, as claimed in claim 21, wherein said irradiating step is carried out using a pulse laser, which is additionally modulated by means of an acousto-optical modulator.

31. The process, as claimed in claim 21, wherein said irradiating step is carried out using a pulse laser, which is additionally modulated by means of a Pockel cell.

32. The process, as claimed in claim 21, wherein said detecting step is carried out using time resolution and wherein said irradiating step is carried out using a multiphoton process.

33. The process, as claimed in claim 32, wherein in said irradiating step, the multiphoton process is second harmonic generation on surfaces.

34. The process, as claimed in claim 32, wherein in said irradiating step, the multiphoton process is two photon excitation.

35. The process, as claimed in claim 21, wherein said irradiating step is carried out using a pulsed near infrared laser.

36. The process, as claimed in claim 21, wherein said irradiating step is carried out using a pulsed near infrared laser, and further comprising the step of:

converting the frequency of the laser downstream to 1 photon excitation.

37. The process, as claimed in claim 21, wherein said irradiating step is carried out using a pulsed near infrared laser, and further comprising the step of:

converting the frequency of the laser downstream to 1 photon excitation of fluorescence.

38. The process, as claimed in claim 21, wherein said detecting step is carried out using phase sensitive detection for improving the signal to noise ratio.

* * * * *